(12) United States Patent
Ishii

(10) Patent No.: US 7,329,431 B2
(45) Date of Patent: Feb. 12, 2008

(54) STENT AND METHOD OF MANUFACTURING STENT

(75) Inventor: Naoki Ishii, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 777 days.

(21) Appl. No.: 10/860,053

(22) Filed: Jun. 4, 2004

(65) Prior Publication Data

US 2004/0249450 A1  Dec. 9, 2004

(30) Foreign Application Priority Data

Jun. 5, 2003 (JP) .............................. 2003-160774

(51) Int. Cl.
*A61L 33/00* (2006.01)
(52) U.S. Cl. .................................... 427/2.24; 623/1.46
(58) Field of Classification Search ............... 623/1.15, 623/1.44, 1.46; 427/2.24, 2.28, 423, 475, 427/476, 477; 428/36.9, 36.91, 447
See application file for complete search history.

(56) References Cited

U.S. PATENT DOCUMENTS

| | | | |
|---|---|---|---|
| 5,242,451 A | 9/1993 | Harada et al. | |
| 5,507,767 A | 4/1996 | Maeda et al. | |
| 5,534,287 A | 7/1996 | Lukic | |
| 5,632,771 A | 5/1997 | Boatman et al. | |
| 5,662,713 A | 9/1997 | Andersen et al. | |
| 5,733,303 A | 3/1998 | Israel et al. | |
| 5,888,201 A | 3/1999 | Stinson et al. | |
| 6,569,195 B2 * | 5/2003 | Yang et al. | 623/1.46 |
| 6,656,217 B1 * | 12/2003 | Herzog et al. | 623/1.15 |

FOREIGN PATENT DOCUMENTS

| | | |
|---|---|---|
| EP | 0 470 246 B1 | 2/1992 |
| EP | 0 623 354 A1 | 11/1994 |
| EP | 0 910 998 A2 | 4/1999 |
| JP | 04-068939 B2 | 11/1992 |
| JP | 05-502179 A | 4/1993 |
| JP | 07-000529 A | 1/1995 |
| JP | 07-500272 A | 1/1995 |
| JP | 08-033718 A | 2/1996 |
| JP | 08-502428 A | 3/1996 |
| JP | 08-507243 A | 8/1996 |

(Continued)

OTHER PUBLICATIONS

G. Spenlehauer et al., "Biodegradable Cisplatin Microspheres Prepared by the Solvent Evaporation Method: Morphology and Release Characteristics", Journal of Controlled Release, 7 (1998), pp. 217-229. Elsevier Science Publishers B.V., Amsterdam, The Netherlands.

*Primary Examiner*—Kevin T. Truong
(74) *Attorney, Agent, or Firm*—Buchanan Ingersoll & Rooney PC

(57) ABSTRACT

A stent to be implanted in a lumen in a living body comprises a stent main body, and a polymer layer provided on a surface of the stent main body, wherein the polymer layer comprises a first biologically/physiologically active substance, and nano- or micro-capsules composed of a first biodegradable polymer and comprising a second biologically/physically active substance therein, and the second biologically/physically active substance is released after the first biologically/physiologically active substance is released to the exterior of the stent.

18 Claims, 3 Drawing Sheets

FOREIGN PATENT DOCUMENTS

| | | |
|---|---|---|
| JP | 09-215753 A | 8/1997 |
| JP | 10-503676 A | 4/1998 |
| JP | 11-221288 A | 8/1999 |
| JP | 2000-501328 A | 2/2000 |
| WO | WO 98/14137 A1 | 4/1998 |

* cited by examiner

STENT AND METHOD OF MANUFACTURING STENT

BACKGROUND OF THE INVENTION

The present invention relates to a stent to be implanted in a stenotic lesion or occluded lesion of a lumen in a living body so as to maintain the stenotic lesion or occluded lesion in an open state. More particularly, the invention relates to a stent capable of releasing sustainedly, or little by little over a long period of time, a biologically/physiologically active substance or substances from a surface of the stent.

In recent years, a medical device called stent for treating a stenotic (constricted) lesion generated in a lumen in a living body, such as blood vessel, bile duct, trachea, esophagus, urethra, etc. has been used. A stent is a hollow tubular medical device which can be implanted in a stenotic lesion or occluded lesion of a lumen such as blood vessel for expanding the stenosis or occluded lesion and maintaining the lumen in an open state, for the purpose of treating a variety of diseases generated by stenosis or occlusion of lumens.

For example, in the case of the coronary artery, a stent is used for preventing the restenosis after percutaneous transluminal coronary angioplasty (PTCA).

By implanting the hollow tubular medical device called stent in a blood vessel after a surgical operation, it has been succeeded to lower the percentages of acute blood vessel occlusion and restenosis. Even where stents have been used, however, it has been recognized by a follow-up after half year and the like that restenosis would occur at the stent implanting lesion in an average ratio of around 20%. Thus, the problem of restenosis is still left to be solved.

Recently, a number of trials have come to be proposed in which a biologically/physiologically active substance such as a carcinostatic agent is loaded on the stent, and the biologically/physiologically active substance is released sustainedly and locally at the lesion where the stent is implanted, in order to lower the percentage of restenosis. For example, a stent in which a surface of a stent main body is coated with a mixture of a therapeutic substance and a polymer has been proposed in JP 8-33718 A. JP 8-33718 A describes a method of manufacturing the stent in which a solution composed of the polymer, the therapeutic substance, and a solvent is applied to the stent main body and then the solvent is evaporated off. In JP 8-33718 A, however, although it is described that the proposed stent is capable of sustainedly release the therapeutic substance and that the therapeutic substance includes both a solid therapeutic substance and a liquid therapeutic substance, it is not investigated to perform sustained release of different therapeutic substances with a large time lag therebetween. According to JP 8-33718 A, therefore, the therapeutic substances which are different from each other are released in substantially the same period. Besides, in the case of sustained release of a therapeutic substance which is extremely toxic to cells such as a carcinostatic agent, it is desirable to sustainedly release the therapeutic substance locally and a number of times, in a small amount at a time, from the viewpoint of suppression of side effects. However, designing of such a sustained therapeutic substance release is very difficult to achieve with the stent proposed by JP 8-33718 A.

JP 5-502179 A describes a stent in which medicaments for restricting occlusion of a blood vessel or the like are contained respectively in two or more polymer layers, and the medicaments are released with a time lag therebetween, wherein the polymer constituting each of the polymer layers is a bio-absorptive polymer. However, such a stent has the problem that, since a number of coating steps are required for forming the respective polymer layers, the manufacturing process is laborious and there would be large scattering among the individual stents manufactured. In addition, the total thickness of the polymer layers is large, which may impair the operating properties of the stent including its capability to reach the lesion.

On the other hand, biodegradable microspheres containing cisplatin therein are manufactured by a solvent evaporation process and are used for drug delivery system and the like (see G. Spenlehauer; M. Vert; J. P. Benoit; F. Chabot; M. Veillard, BIODEGRADABLE CISPLATIN MICROSPHERES PREPARED BY THE SOLVENT EVAPORATION METHOD: MORPHOLOGY AND RELEASE CHARACTERISTICS, "Journal of Controlled Release", Elsevier Science Publishers B. V., Amsterdam, 1988, 7, pp. 217-229).

SUMMARY OF THE INVENTION

Accordingly, it is an object of the present invention to provide a stent which makes it possible to design a sustained release of biologically/physiologically active substances over a long period of time without spoiling the operating property of the stent and which is easy to manufacture.

The above object is attained by the present invention residing in the followings (1) to (10):

(1) A stent to be implanted in a lumen in a living body, the stent comprising a hollow cylindrical stent main body which is open at both terminal end portions thereof and extends in the longitudinal direction between the two terminal open portions, and a polymer layer provided on a surface of the stent main body, wherein the polymer layer comprises a first biologically/physiologically active substance, and first nano- or micro-capsules composed of a first biodegradable polymer and comprising a second biologically/physiologically active substance therein, and the second biologically/physiologically active substance is released after the first biologically/physiologically active substance is released to the exterior of the stent.

(2) A stent according to the above paragraph (1), wherein the polymer constituting the polymer layer is a water- or water vapor-permeable polymer.

(3) A stent according to the above paragraph (1) or (2), wherein the stent main body is formed of a metallic material.

(4) A stent according to the above paragraph (1) or (2), wherein the stent main body is formed of a polymeric material.

(5) A stent according to any one of the above paragraphs (1) to (4), wherein the polymer constituting the polymer layer is at least one selected from the group consisting of silicone-based polymers, vinyl-based polymers, cellulose-based polymers, polyurethanes, polyesters, acrylic polymers, thermoplastic elastomers, biodegradable polymers, and bio-derived polymers.

(6) A stent according to any one of the above paragraphs (1) to (5), wherein the first biologically/physiologically active substance and the second biologically/physiologically active substance are different from each other.

(7) A stent according to any one of the above paragraphs (1) to (6), wherein the polymer layer further comprises second nano- or micro-capsules composed of a second biodegradable polymer being lower than the first biodegradable polymer in degradation rate and comprising a third biologically/physiologically active substance therein, and the third biologically/physiologically active substance is released after the second biologically/physiologically active substance is released.

(8) A stent according to any one of the above paragraphs (1) to (7), wherein the first and second biodegradable polymers composing the first and second nano- or micro-capsules each comprise at least one selected from the group consisting of polylactic acid, polyglycolic acid, polycaprolactone, polyhydroxy butyrate, and copolymers thereof.

(9) A stent according to any one of the above paragraphs (1) to (8), wherein the first, second and third biologically/physiologically active substances each comprise at least one selected from the group consisting of carcinostatic agent, immunosuppressant, antibiotic, antirheumatic, antithrombic agent, antihyperlipemic agent, ACE inhibitor, calcium antagonist, integrin inhibitor, antiallergic agent, antioxidant, GPIIb IIIa antagonist, retinoid, flavonoid, carotenoid, lipid improver, DNA synthesis inhibitor, tyrosine kinase inhibitor, antiphlogistic, bio-derived material, and interferon.

(10) A stent according to above paragraph (7), wherein the first biologically/physiologically active substance is a biologically/physiologically active substance for suppressing thrombus deposition and reducing inflammation, the second biologically/physiologically active substance is a biologically/physiologically active substance for restraining the propagation of smooth muscle cells, and the third biologically/physiologically active substance is a biologically/physiologically active substance for promoting NO production and blood vessel endothelial cell adhesion, whereby a lesion of a blood vessel where the stent is implanted can be maintained in an open state.

(11) A method of manufacturing a stent according to the above paragraph (1), the method comprising the steps of: dispersing the first biologically/physiologically active substance and the first nano- or micro-capsules composed of the first biodegradable polymer and comprising the second biologically/physiologically active substance therein, in a liquid-state polymer; bringing a surface of the stent main body into contact with the liquid-state polymer; and substantially fixing the polymer to the stent main body.

A stent according to the present invention is a stent to be implanted in a lumen in a living body, the stent comprising a stent main body and a polymer layer provided on a surface of the stent main body. In the stent according to the present invention, the polymer layer comprises a first biologically/physiologically active substance, and first nano- or micro-capsules composed of a first biodegradable polymer and comprising a second biologically/physiologically active substance therein, whereby the second biologically/physiologically active substance comprised in the first nano- or micro-capsules is released after the first biologically/physiologically active substance is released to the exterior of the stent.

Therefore, the stent according to the present invention can be locally applied directly to a lumen in a living body, and, by use of the stent according to the present invention, biologically/physiologically active substances can be sustainedly released in an effective manner with a lapse of time, at the time of blood vessel remodeling. For example, by use of the stent according to the present invention, it is possible to restrain thrombus deposition and reduce inflammation in an initial period, to restrain propagation of smooth muscle cells in a middle period, and to promote NO production and endothelial cell adhesion in a latter period, thereby securely preventing restenosis of the stenotic lesion or occluded lesion.

BRIEF DESCRIPTION OF THE DRAWINGS

The above and other objects, features and advantages of the present invention will become apparent from the following description and appended claims, taken in conjunction with the accompanying drawings, in which:

DESCRIPTION OF THE PREFERRED EMBODIMENTS

Now, the stent according to the present invention will be described in detail below, based on some preferred embodiments shown in the accompanying drawings.

The stent of the present invention comprises a stent main body, and a polymer layer provided on a surface of the stent main body.

Figure 1:
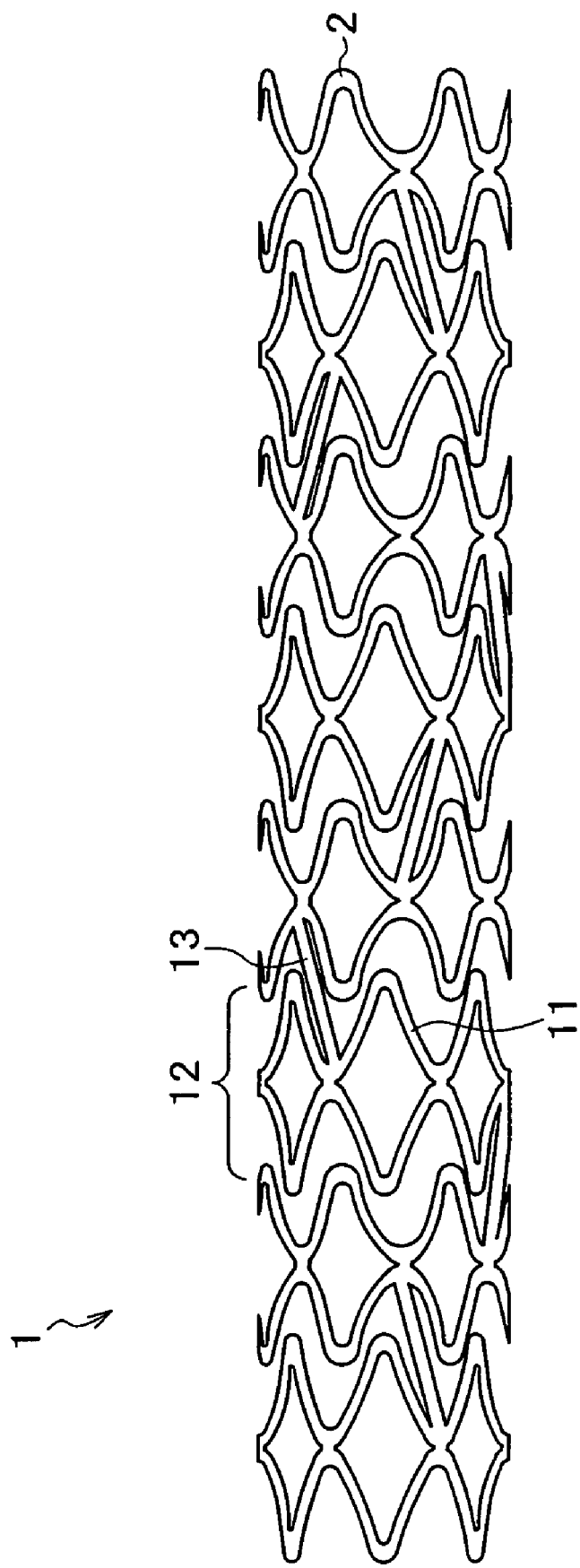
FIG. 1 is a perspective view showing one embodiment of the stent according to the present invention.
Figure 2:
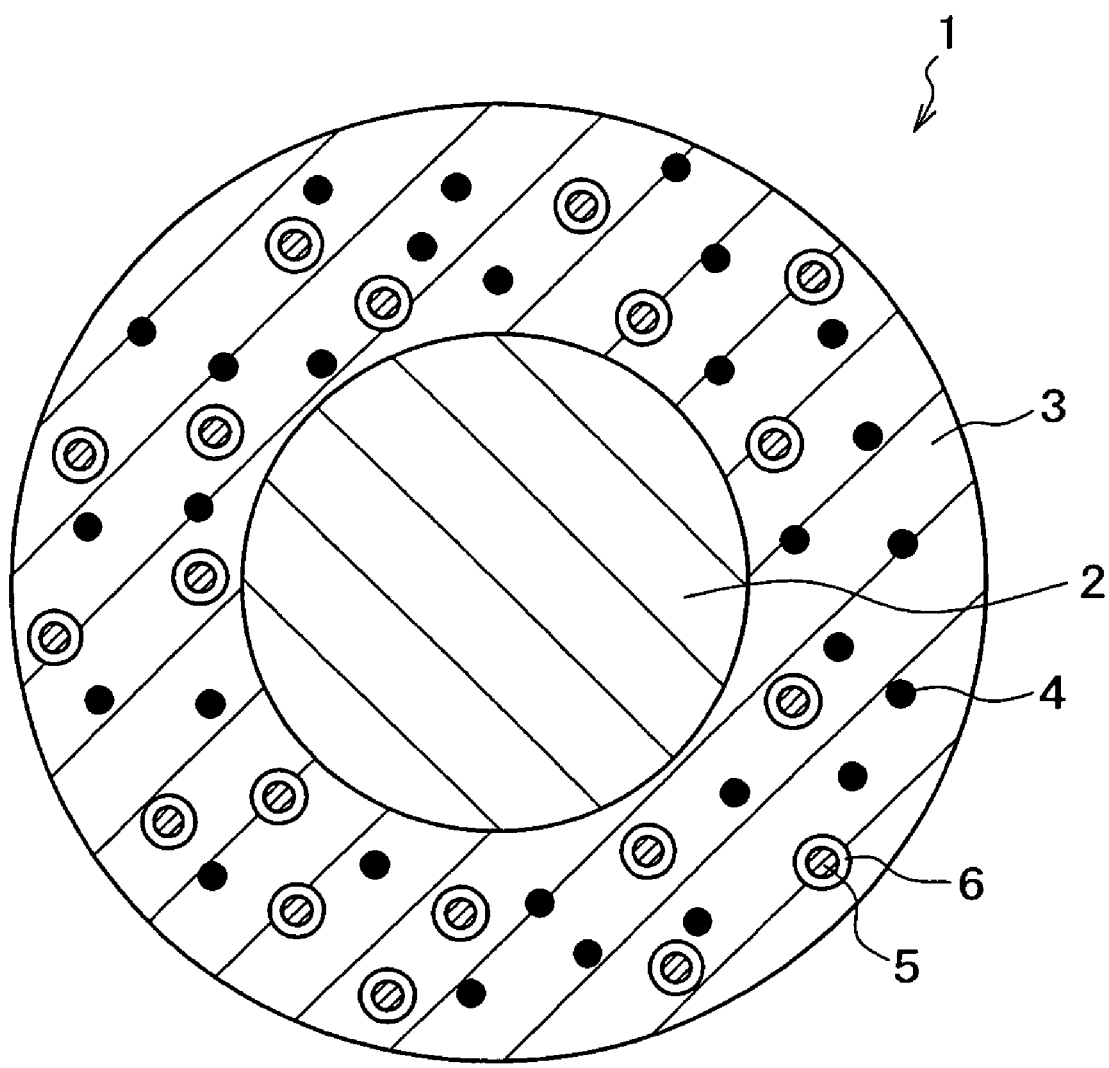
FIG. 2 is a cross-sectional view of a filamentous member of the stent of FIG. 1.

FIG. 1 is a perspective view showing one embodiment of the stent according to the present invention, FIG. 2 is a cross-sectional view of a filamentous member of the stent of FIG. 1.

As shown in FIGS. 1 and 2, the stent 1 according to the present invention comprises a polymer layer 3 formed on a surface of a filamentous member 2 constituting a stent main body, so as to cover the filamentous member 2, the polymer layer 3 comprising a first biologically/physiologically active substance 4 and first nano- or micro-capsules 6 which are composed of a first biodegradable polymer and comprise a second biologically/physiologically active substance 5 therein. Here, the polymer layer 3 may not necessarily cover the entire surface of the filamentous member 2 constituting the stent main body, and it suffices for the polymer layer 3 to cover at least a part of the surface of the filamentous member 2 constituting the stent main body. Therefore, only the surface portions of the filamentous member 2 corresponding to the outside surface of the stent main body, which is cylindrical in shape, may be covered with the polymer layer 3, or, on the contrary, only the surface portions of the filamentous member 2 corresponding to the inside surface of the stent main body may be covered with the polymer layer 3.

For example, in the case of using an antiphlogistic as a biologically/physiologically active substance, it suffices that the surface portions of the filamentous member 2 corresponding to the outside surface of the stent main body which is brought into contact with the inner surface of a lumen are covered with the polymer layer 3.

The thickness of the polymer layer 3 is not particularly limited, and is preferably in the range of 0.1 to 50 μm, more preferably 1 to 10 μm.

The stent main body is a hollow cylindrical body which is open at both terminal end portions thereof and which extends in the longitudinal direction between the two terminal end portions. The side surface of the hollow cylindrical body has a multiplicity of cutout portions communicating between the outside surface and the inside surface thereof so that the hollow cylindrical body can be expanded and contracted in the radial direction thereof through deformation of the cutout portions. The hollow cylindrical body, or stent main body, is to be implanted in a vessel such as a blood vessel or a body lumen such as the bile duct, thereby maintaining the shape thereof.

In the embodiment illustrated in FIG. 1, the fundamental unit of the stent main body is a roughly rhombic element 11 which is composed of the filamentous member 2 and has a cutout portion therein. A plurality of the roughly rhombic elements 11 are arranged in series in the minor-axis direction and connected to each other, thereby constituting an annular unit 12. Each annular unit 12 is connected to the adjacent annular units through filamentous connection members 13. As a result, a plurality of the annular units 12 are arranged continuously in the axial direction thereof in a partly joined condition.

In the present invention, the stent main body is not limited to the embodiment shown in the figure but widely includes those structures in which a hollow cylindrical body being open at both terminal end portions thereof and extending in the longitudinal direction between the two terminal end portions is provided in its side surface with a multiplicity of cutout portions communicating between the outside surface and the inside surface thereof so that the hollow cylindrical body can be expanded and contracted in the radial direction thereof through deformation of the cutout portions.

The stent main body is a medical device formed of a metallic material or a polymeric material, and a variety of forms of stent main body have been proposed, including those in which a hollow tubular body formed of a metallic material or a polymeric material is provided with pores in its side surface, and those in which wires of a metallic material or fibers of a polymeric material are knitted into the shape of a hollow cylinder.

Specific examples of the stent main body having such a structure capable of expansion and contraction in the radial direction thereof include: a stent main body in which an elastic filamentous material is bent in a coil form and a plurality of the coil-formed members are connected to each other into a hollow cylindrical shape so that the gapes between the elastic filamentous materials constitute cutout portions, as disclosed in JP 9-215753 A and JP 7-529 A; a stent main body in which an elastic filamentous material is bent in a zigzag form and a plurality of the zigzag-formed members are connected to each other into a hollow cylindrical shape so that the gaps between the elastic filamentous materials constitute cutout portions, as disclosed in JP 8-502428 A and JP 7-500272 A; a stent main body in which an elastic filamentous material is bent into the shape of a snaky flat ribbon and the bent member is helically wound around a mandrel into a hollow cylindrical shape so that the gaps between the elastic filamentous materials constitute cutout portions, as disclosed in JP 2000-501328 A and JP 11-221288 A; a stent body having a mesh-like structure, as disclosed in JP 10-503676 A, and a stent main body in which a plate-like member is bent in a coil form into a hollow cylindrical shape so that the gaps between the adjacent coil portions constitute cutout portions, as disclosed in JP 8-507243 A. In addition, JP 4-68939 B exemplifies a plurality of hollow cylindrical stent main bodies having different structures, including a stent main body in which an elastic plate-like member is bent spirally into a hollow cylindrical shape so that the gaps between the adjacent spiral portions constitute cutout portions, a stent main body in which an elastic filamentous material is braided into a hollow cylindrical shape so that the gaps between the elastic filamentous materials constitute cutout portions, etc. Other than the foregoing, the stent main body may be in the shape of a leaf spring coil, a multiple spiral, a deformed tube, or the like. Besides, JP 4-68939 B describes, in FIGS. 2(a) and 2(b), a stent main body in which an elastic plate-like member is bent in vortex form into a hollow cylindrical shape; such a hollow cylindrical stent main body which does not have cutout portions in the side surface of the hollow cylindrical body but can be expanded and contracted in the radial direction of the hollow cylindrical body can also be used as the stent main body in the present invention. All the references and patent applications cited herein are hereby incorporated by reference.

The size of the stent main body may be appropriately selected according to the application site (the site where the stent is applied). For example, where the stent main body is applied to the coronary artery, it is generally preferable that the stent main body has an outside diameter before expansion of 1.0 to 3.0 mm and a length of 5 to 50 mm.

Where the stent main body is composed of a filamentous member as above-mentioned, the length in the width direction of the filamentous member for constituting the stent main body having a multiplicity of cutout portions is preferably 0.01 to 0.5 mm, more preferably 0.05 to 0.2 mm.

The method for manufacturing the stent main body is not particularly limited, and may be appropriately selected from conventional manufacturing methods in the art, according to the structure and the material of the stent.

Examples of the material for the stent main body include polymeric materials, metallic materials, carbon fibers, ceramics, etc. The material is not particularly limited, inasmuch as it has certain degrees of rigidity and elasticity, but it is preferable for the material to be compatible with living bodies.

Specifically, usable examples of the polymeric material include polyolefins such as polyethylene, and polypropylene; polyesters such as polyethylene terephthalate; cellulose-based polymers such as cellulose acetate, and cellulose nitrate; fluoropolymers such as polyterafluoroethylene, and tetrafluoroethylene-ethylene copolymer; etc. Usable examples of the metallic material include stainless steels, tantalum, titanium, nickel-titanium alloys, tantalum-titanium alloys, nickel-aluminum alloys, Inconel, gold, platinum, iridium, tungsten, and cobalt-based alloys. Among stainless steels, preferred is SUS316L from the view point of the corrosion resistance.

The stent main body can be suitably formed from a material which is appropriately selected from the above-mentioned materials according to the application site or the expansion means. For example, where the stent main body is formed of a metallic material, the stent can be securely implanted in the lesion because of its excellent strength. Where the stent main body is formed of a polymeric material, the polymeric material can reach or be delivered to the lesion without difficulty because of its excellent flexibility.

In addition, where the stent is of the self-expansion type, a restoring force for returning to an original shape (expanded shape) is needed, so that superelastic alloys such as titanium-nickel alloy are preferably used. Where the stent is of the balloon expansion type, it is necessary that original (pre-expanded) shape restoration after expantion of the stent would not easily occur, and, therefore, stainless steels or the like are preferably used.

Besides, where the stent main body is formed of carbon fibers, the stent shows a high strength, an excellent flexibility, and high safety in living bodies.

The expansion means for the stent main body is not particularly limited, and may be of the self-expansion type, namely, the type in which when a force holding the stent main body in a folded state in the radial direction is removed, the stent main body expands in the radial direction by its own restoring force, or may be of the balloon expansion type, namely, the type in which a balloon is expanded inside the stent main body so that the stent main body is expanded in the radial direction by the external force exerted by the balloon.

Setting of a balloon expansion type stent to implant in a lesion is carried out by inserting the stent into the lesion by use of a catheter, then locating a balloon inside the stent, and expanding the balloon so that the stent is expanded (elastically deformed) by the expanding force of the balloon, whereby the stent is brought into close contact with and fixed to the inside surface of the lesion.

In the case of a self-expansion type stent, the stent in a folded state in the radial direction is inserted into the lesion, and then the stress exerted on the stent for keeping it in the folded state is removed. For example, the stent in a contracted state is contained in a tube having an outside diameter smaller than the inside diameter of the lesion, the distal end of the tube is brought to the lesion, and then the stent is pushed out of the tube. The stent thus pushed out is simultaneously released from the stress having been exerted thereon, and the stent expands in the manner of restoring its shape before folding. As a result, the stent is brought into close contact with and fixed to the inside surface of the living organ (e.g., blood vessel) at the lesion.

The polymer layer 3 of the stent according to the present invention comprises, in a base polymer, a first biologically/physiologically active substance 4, and first nano- or micro-capsules 6 composed of a first biodegradable polymer and comprising a second biologically/physiologically active substance 5 therein.

In present description, nano- or micro-capsules of biodegradable polymer are biodegradable polymer particles having a particle diameter of less than 10 μm, in which a biologically/physiologically active substance is comprised therein.

Here, the word "nano- or micro-capsules" covers first nano- or micro-capsules and second nano- or micro-capsules mentioned below.

The size of the nano- or micro-capsule is set within such a range as not to markedly impair the performances of the stent main body such as its capability to reach (to be delivered) to the lesion and low-irritativeness to the blood vessel wall. The particle diameter of the nano- or micro-capsules is preferably not more than 5 μm, more preferably in the range of 3 to 0.01 μm, and most preferably 1 to 0.05 μm.

The nano- or micro-capsules are biodegradable polymer particles comprising a biologically/physiologically active substance therein, which are obtained by preparing a solution containing the biologically/physiologically active substance (to be contained in the nano- or micro-capsules) and a biodegradable polymer dissolved in a hydrophobic solvent, emulsifying the solution in an aqueous solution containing a dispersant such as polyvinyl alcohol, and sufficiently stirring the resultant emulsion under room temperature, normal pressure, and light-shielded conditions (in dark).

The biodegradable polymer particles thus obtained are preferably subjected further to centrifugal separation for solvent removal, washing with distilled water, freeze drying, and sieving so as to obtain particles not greater than a predetermined particle diameter, before use.

The nano- or micro-capsules are dispersed in a solvent containing the base polymer and the biologically/physiologically active substance which have been prepared separately, and the resultant dispersion is applied to the stent main body. The method for applying the dispersion to the stent main body is not particularly limited; specific examples of the method include coating (application), spraying, and immersion.

Figure 3:
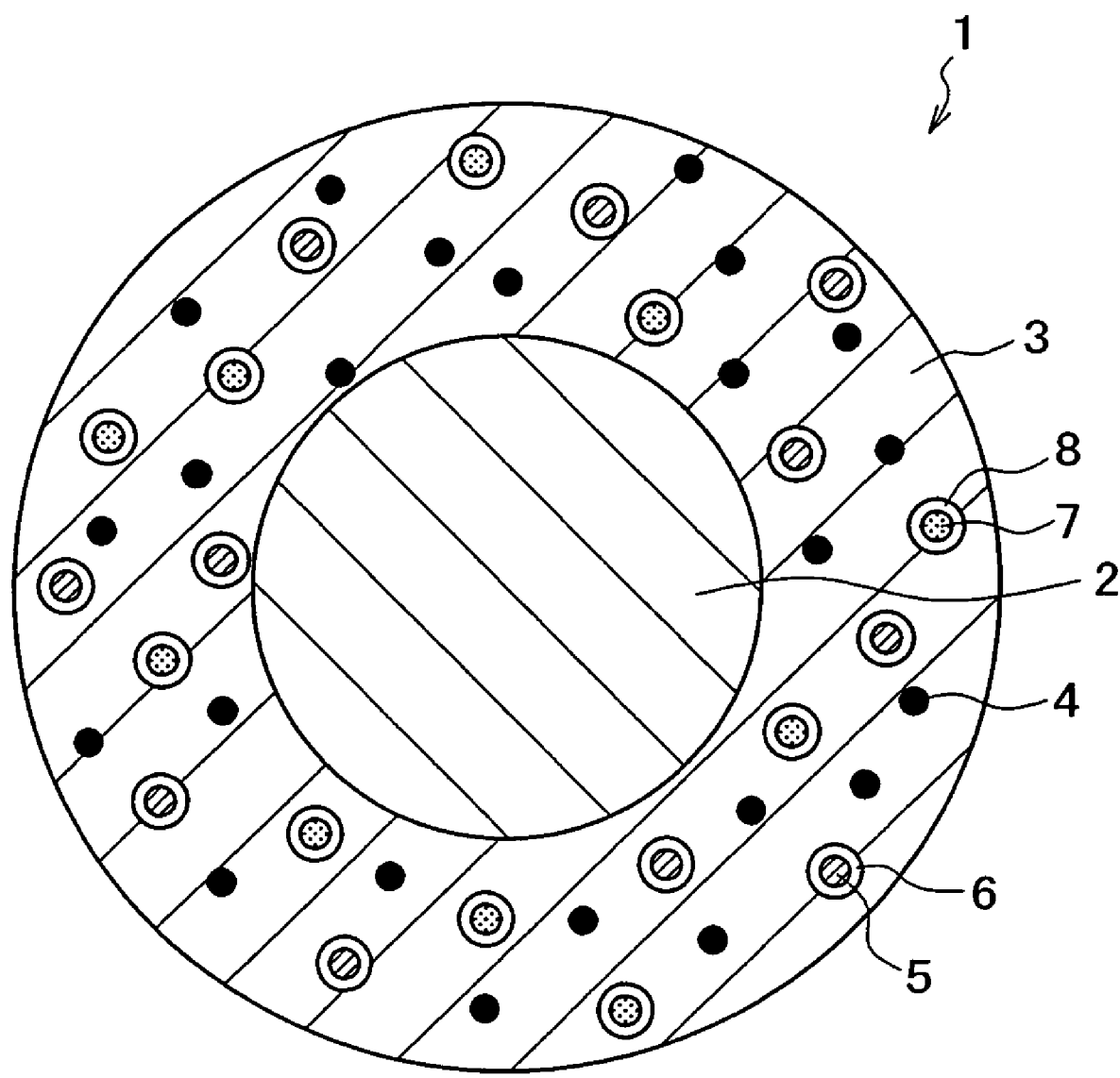
FIG. 3 is a cross-sectional view of a filamentous member showing another embodiment of the stent according to the present invention.

FIG. 3 is a cross-sectional view of a filamentous member illustrating another embodiment of the stent according to the present invention. The stent 1 of FIG. 3 is the same as the stent 1 of FIGS. 1 and 2 except that the polymer layer 3 further comprises second nano- or micro-capsules 8 in addition to the first biologically/physiologically active substance 4 and the first nano- or micro-capsules 6. The second nano- or micro-capsules 8 are composed of a second biodegradable polymer and comprise a third biologically/physiologically active substance 7 therein. The first biodegradable polymer composing the first nano- or micro-capsules 6 and the second degradable polymer composing the second nano- or micro-capsules 8 are different from each other in degradation rate. More particularly, the second degradable polymer is lower than the first degradable polymer in degradation rate.

In the stent of FIG. 3, in addition to the first biologically/physiologically active substance 4 and the first nano- or micro-capsules 6, the second nano- or micro-capsules 8 composed of the second degradable polymer and comprising the third biologically/physiologically active substances therein are prepared by a similar method, then the first and second nano- or micro-capsules 6, 8 comprising respectively the second and third biologically/physiologically active substances are dispersed in the solvent containing the first biologically/physiologically active substance and the base polymer, and the resultant dispersion is applied to the stent main body, before use.

In the stent according to the present invention, the number of the nano- or micro-capsules are not particularly limited to the embodiment described above. For example, third, fourth or other nano- or micro-capsules each composed of a degradable polymer and comprising a biologically/physiologically active substance may be comprised in the polymer layer. In this case, the degradable polymers composing the nano- or micro-capsules are different from each other and also from the first and second the degradable polymers in degradation rate.

Examples of the biodegradable polymer for forming the nano- or micro-capsules include polylactic acid, polyglycolic acid, polycaprolactone, polyhydroxy butyrate, and copolymers thereof. Among these examples, preferred are polylactic acid, polyglycolic acid, and lactic acid-glycolic acid copolymer because these polymers are preferable in the control of hydrolysis rate and are known well as preferred implant material. From the viewpoint of control of sustained release, the lactic acid-glycolic acid copolymer is most preferably used.

By selection of the biodegradable polymer for forming the nano- or micro-capsules, it is possible to control the rate of degradation of the biodegradable polymer in a living body. As described above, in the stent 1 of FIG. 3, the second degradable polymer composing the second nano- or micro-capsules 8 is lower than the first degradable polymer composing the first nano- or micro-capsules 6 in degradation rate. With this setting, the timings of the release of the second biologically/physiologically active substances comprised in the first nano- or micro-capsules 6 and third biologically/physiologically active substances comprised in the second nano- or micro-capsules 8 to the exterior of the stent 1 can be staggered from each other. More particularly, the third biologically/physiologically active substance comprised in the second nano- or micro-capsules 8 is released after the second biologically/physiologically active substance comprised in the first nano- or micro-capsules 6 is released.

To obtain biodegradable polymers being different from each other in degradation rate, the biodegradable polymers being of the same species but differing in molecular weight may be selected or the biodegradable polymers being different from each other in species may be selected. For example, where biodegradable polymers being of the same species but differing in molecular weight are selected as the first and second biodegradable polymers, the biodegradable polymer with a lower molecular weight is first degraded in the living body, and the biodegradable polymer with a higher molecular weight is then degraded in the living body with a delay. In a specific exemplary case where polylactic acid is used as the biodegradable polymer, polylactic acid with a molecular weight Mw=1500 to 2000 is used for composing the first nano- or micro-capsules 6 comprising the second biologically/physiologically active substance 5 therein, while polylactic acid with a molecular weight Mw=50000 to 150000 is used for composing the nano- or micro-capsules 8 comprising the third biologically/physiologically active substance 7 therein. When a blend of polyglycolic acid and polylactic acid or a copolymer of glycolic acid and lactic acid, which has a low degradation rate, is selected as the biodegradable polymer, the timing(s) of release of the biologically/physiologically active substance(s) to the exterior of the stent can be further delayed.

The first and second biologically/physiologically active substances may be the same or different. Where they are the same, it is possible to design a sustained release mode similar to the process of locally injecting the biologically/physiologically active substance twice. Where they are different from each other, it is possible to optimally injecting the biologically/physiologically active substance according to the variation of the symptom of the lesion with time.

The third biologically/physiologically active substances may be the same or different from the first and second biologically/physiologically active substances. Where they are the same, it is possible to design a sustained release mode similar to the process of locally injecting the biologically/physiologically active substance thrice. Where they are different from each other, it is possible to optimally injecting the biologically/physiologically active substances according to the variation of the symptom of the lesion with time.

The polymer for constituting the polymer layer 3 comprising the first biologically/physiologically active substance 4, the first nano- or micro-capsules 6 and the second nano- or micro-capsules 8 therein is preferably a water- or water vapor-permeable polymer, examples of which include bio-compatible polymers, such as silicone-based polymers, vinyl-based polymers, cellulose-based polymers, polyurethane, polyesters, acrylic polymers, and thermoplastic elastomers; biodegradable polymers, and bio-derived polymers. Among these examples, preferred are those polymers which are soluble in poor solvents for the biodegradable polymer used to comprise the biologically/physiologically active substance(s) and which show a high stability in living bodies, such as silicone elastomers, ethylene-vinyl acetate copolymer, carbonate-based polyurethane, and cross-linked products of bio-derived materials capable of control of water (moisture) content. Where the polymer for forming the polymer layer 3 is compatible with living bodies, the polymer preferably has a water vapor permeability, which is an index of water- or water vapor-permeableness, of not less than $1 \times 10^{-8}$ [cm$^3$(STP) (cm·s·cmHg)$^{-1}$]. If the water- or water vapor-permeableness of the polymer constituting the polymer layer 3 is extremely low, the hydrolysis of the biodegradable polymer comprised in the polymer layer 3 would be hindered, which may make it impossible to control the sustained release of the biologically/physiologically active substance(s) comprised in the biodegradable nano- or micro-capsules.

The silicone elastomers widely include elastomer compositions consisting principally of dialkylpolysiloxanes; they include not only those of the straight chain type but also those which have branched chains, those which contain vinyl groups, those in which part of alkyl groups are substituted by hydrogen atoms, and those which are amino-modified or halogen-modified. It should be noted here that not less than 90% of the alkyl groups constituting the dialkylpolysiloxane are methyl groups. In addition, the viscosity of the silicone elastomers before curing is not less than 500 cps, and the hardness of the silicone elastomers after curing is in the range of 20 to 80 Durometer Hardness, Shore A. Incidentally, two-part type silicone elastomers are preferred, in view of easiness of handling in forming the polymer layer. The silicone elastomers fulfilling the above-mentioned conditions may be commercial products, preferable examples of which include the silicone elastomer available from DOW CORNING under the trade name SILATIC, and the silicone elastomer available from Nusi under the trade name SILICONE Elastomer (MED-4211).

The ethylene-vinyl acetate copolymer preferably has a weight ratio of ethylene to vinyl acetate of from 60:40 to 95:5 and a melt flow rate (MFR) of from 1 to 60 g/10 min.

The biologically/physiologically active substances are not particularly limited, but they preferably are those which have an effect of preventing restenosis of the stenotic lesion or occuluded lesion when the stent according to the present invention is implanted in a lesion of a body lumen. Specific examples of the biologically/physiologically active substances include carcinostatic agents, immunosuppressants, antibiotics, antirheumatics, antithrombus agents, antihyperlipemic agents, ACE inhibitors, calcium antagonists, integrin inhibitors, antiallergic agents, antioxidants, GPIIb IIIa antagonists, retinoids, flavonoids, carotenoids, lipid improvers, DNA synthesis inhibitors, tyrosine kinase inhibitors, antiphlogistics, bio-derived materials, and interferon. Among these, carcinostatic agents such as paclitaxel are used most preferably, from the viewpoints of dose and drug efficacy.

Specific preferable examples of the carcinostatic agent include vincristin sulfate, vinblastin sulfate, vindecin sulfate, irinotecan hydrochloride, paclitaxel, docetaxel hydrate, methotrexate, and cyclophosphamide.

Specific preferable examples of the immunosuppressant include sirolimus, tacrolimus hydrate, azathioprine, cyclosporine, mofetil mycophenolate, gusperimus hydrochloride, and mizoribine.

Specific preferable examples of the antibiotic include mitomycin C, doxorubicin hydrochloride, actinomycin D, daunorubicin hydrochloride, idarubicin hydrochloride, pirarubicin hydrochloride, aclarubicin hydrochloride, epirubicin hydrochloride, peplomycin sulfate, and zinostatin stimalamer.

Specific preferable examples of the antirheumatic include sodium aurothiomalate, penicillamine, and lobenzarit disodium.

Specific preferable examples of the antithrombic agent include heparin, ticlopidine hydrochloride, and hirudin.

Specific preferable examples of the antihyperlipemic agent include HMG-CoA reductase inhibitors and probucol.

More specific preferred examples of the HMG-CoA reductase inhibitors include cerivastatin sodium, atoruvastatin, nisvastatin, pitavastatin, fluvastatin sodium, simvastatin, lovastatin, and pravastatin sodium.

Specific preferable examples of the ACE inhibitor include quinapril hydrochloride, perindopril erbumine, trandolapril, cilazapril, temocapril hydrochloride, delapril hydrochloride, enalapril maleate, lisinopril, and captopril.

Specific preferable examples of the calcium antagonist include nifedipine, nilvadipine, diltiazem hydrochloride, benidipine hydrochloride, and nisoldipine.

Specific preferable examples of the antiallergic agent include tranilast.

Specific preferable examples of the retinoid include all-trans-retinoic acid.

Specific preferable examples of the antioxidant include catechins, anthocyanins, proanthocyanidin, lycopene, and β-carotene. Among the catechins, particularly preferred is epigallocatechin gallate.

Specific preferable examples of the tyrosine kinase inhibitor include genistein, tryphostin, and apstatin.

Specific preferable examples of the antiphlogistic include steroids such as dexamethasone, prednisolone, etc., and aspirin.

Specific preferable examples of the bio-derived material include EGF (epidermal growth factor), VEGF (vascular endothelial growth factor), HGF (hepatocyte growth factor), PDGF (platelet derived growth factor), and BFGF (basic fibroblast growth factor).

When the stent according to the present invention is implanted in the target lesion, the first biologically/physiologically active substance comprised in the polymer layer is released to the exterior of the stent. Simultaneously or thereafter, the first nano- or micro-capsules comprising the second biologically/physiologically active substance are also released. The degradation of the first biodegradable polymer composing the first nano- or micro-capsules proceeds gradually, so that the second biologically/physiologically active substance comprised in the first nano- or micro-capsules is released, in a pulse manner, to the exterior of the stent with a delay behind the release of the first biologically/physiologically active substance. It suffices that the timing of the start of release of the second biologically/physiologically active substance is after the start of release of the first biologically/physiologically active substance, and the release of the second biologically/physiologically active substance may be started before the first biologically/physiologically active substance has been completely released. The term "in a pulse manner" herein means that the release condition transfers, with the lapse of time, from a release condition where the second biologically/physiologically active substance is released in an amount of less than 50% when the first biologically/physiologically active substance is released in an amount of not less than 50% to a release condition where both the first biologically/physiologically active substance and the second biologically/physiologically active substance are released in amounts of not less than 50%.

Specifically, for example, the first biologically/physiologically active substance is released in an amount of not less than 80% whereas the second biologically/physiologically active substance is released in an amount of less than 5% after one day from the time when the stent is implanted in the lesion; the first biologically/physiologically active substance is released in an amount of not less than 95% whereas the second biologically/physiologically active substance is released in an amount of less than 10% after three days; the first biologically/physiologically active substance is released in an amount of not less than 95% whereas the second biologically/physiologically active substance is released in an amount of less than 50% after seven days; and the first biologically/physiologically active substance is released in an amount of not less than 95% whereas the second biologically/physiologically active substance is released in an amount of not less than 80% after 14 days.

Furthermore, where the biologically/physiologically active substances are comprised in a plurality of kinds of nano- or micro-capsules composed of different biodegradable polymers respectively such as the stent 1 of FIG. 3, the timings of the releases of the biologically/physiologically active substances to the exterior of the stent can be staggered each other. In other words, where only one kind of biologically/physiologically active substance is used, it is possible to release the biologically/physiologically active substance in a mode similar to the process of locally injecting the same biologically/physiologically active substance a number of times, in a small amount at a time; on the other hand, where a plurality of kinds of biologically/physiologically active substances are used, it is possible to select and inject the biologically/physiologically active substances according to the variation of symptom of the lesion with time.

The selection of the biologically/physiologically active substances is not particularly limited, and there are a variety of possible combinations. In one example, in order to achieve sustained release of biologically/physiologically active substances in an effective manner on a time lapse basis at the time of blood vessel remodeling after implanting the stent, an antiphlogistic, an antithrombic agent or the like is comprised as the first biologically/physiologically active substance 4 in the polymer layer 3 for the purpose of restraining thrombus deposition and reducing inflammation, while a carcinostatic agent, an immunosuppressant, an ACE inhibitor or the like is comprised as the second biologically/physiologically active substance 5 in the former-period sustained release type nano- or micro-capsules, that is the first nano- or micro-capsules 6, for the purpose of restraining the propagation of smooth muscle cells, and an HMG-CoA reductase inhibitor or the like is comprised as the third biologically/physiologically active substance 7 in the latter-period sustained release type nano- or micro-capsules, that is the second nano- or micro-capsules 8 for the purpose of promoting NO production and blood vessel endothelial cell adhesion. In such a manner, it is possible to select the biologically/physiologically active substances and to design the sustained release mode.

Besides, in the case of a highly toxic biologically/physiologically active substance such as carcinostatic agent, it is effective to inject the biologically/physiologically active substance a number of times, in a small amount at a time. In view of this, by applying a carcinostatic agent as the first, second, and third biologically/physiologically active substances to the stent according to the present invention, it is possible to control the injection amount (dose) and the injection timing of the carcinostatic agent.

EXAMPLES

Now, the present invention will be described more in detail below referring to Examples, which are not limitative of the invention.

Example 1

First, a 1.0 wt % solution of ethylene-vinyl acetate copolymer (vinyl acetate: 40%) in tetrahydrofuran (THF) was prepared, to which dexamethasone as an antiphlogistic was added in an amount of 30 wt % based on the ethylene-vinyl acetate copolymer, to obtain a solution. Separately, a solution was prepared by dissolving 1 g of paclitaxel and 1 g of polylactic acid with Mw=2,000 in 10 ml of methylene chloride, then the solution was emulsified in 100 ml of a 2 wt % aqueous solution of polyvinyl alcohol (PVA), and the emulsion was subjected to sonication under the conditions of room temperature and 15 W for 10 min. The resultant solution was slowly stirred by a magnetic stirrer under room temperature, normal pressure, and light-shielded conditions for 15 hr to completely evaporate off methylene chloride, thereby obtaining micro-capsules (oil-in-water method). The micro-capsules obtained were subjected to centrifugal separation at 10,000 revolutions/hr, were washed with distilled water thrice, and were freeze dried. Further, the micro-capsules were sieved to trap only the micro-capsules having a diameter of 5 μm or below.

The micro-capsules were dispersed in the THF solution of the ethylene-vinyl acetate copolymer containing dexamethasone, and the resultant solution was sprayed onto a stent main body formed of stainless steel (SUS316L) shown in FIG. 1, to produce a sample. In this case, the thickness of the polymer layer was 10 μm.

The stent thus obtained was served to a sustained release test of the biologically/physiologically active substances. The sustained release test was carried out by immersing the obtained stent in 10 ml of a 4% bovine serum albumin (BSA) added RO water at 37° C., performing sampling periodically, and performing determination by high-performance liquid chromatography (HPLC). The determination was carried out by use of a preliminarily formed calibration curve.

The results are shown in Table 1. Incidentally, the release amount of the biologically/physiologically active substance in Table 1 is in terms of the ratio (%) to the mass of the biologically/physiologically active substance loaded on the stent main body.

Example 2

First, a 1.0 wt % solution of a silicone elastomer (two-part silicone Q7-4840) in tetrahydrofuran (THF) was prepared, to which dexamethasone as an antiphlogistic was added in an amount of 30 wt % based on the silicone elastomer, to prepare a solution. Separately, a solution was prepared by dissolving 1 g of paclitaxel and 1 g of polylactic acid with Mw=2,000 in 10 ml of methylene chloride, and the solution was emulsified in 100 ml of a 2 wt % aqueous solution of polyvinyl alcohol (PVA), and the emulsion was subjected to sonication under the conditions of room temperature and 15 W for 10 min. The resultant solution was stirred slowly by a magnetic stirrer under room temperature, normal pressure, and light-shielded conditions for 15 hr, to completely evaporate off methylene chloride, thereby obtaining micro-capsules (oil-in-water method). The micro-capsules thus obtained were subjected to centrifugal separation at 10,000 revolutions/hr, were then washed with distilled water thrice, and were freeze dried. The micro-capsules were sieved to trap only the micro-capsules having a diameter of 5 μm or below.

Micro-capsules comprising simvastatin were prepared in the same manner as above, except that polylactic acid with Mw=100,000 was used.

The two kinds of micro-capsules obtained above were dispersed in the THF solution of the silicone elastomer comprising dexamethasone, and the resultant solution was sprayed onto a stent main body formed of stainless steel (SUS316L) shown in FIG. 1, followed by a heat treatment at 80° C. for 16 hr for the purpose of curing the silicone, to obtain a sample. In this case, the thickness of the polymer layer was 10 μm.

The stent thus obtained was served to a sustained release test of the biologically/physiologically active substances in the same manner as in Example 1.

The results are shown in Table 1. Incidentally, the release amount of the biologically/physiologically active substance in Table 1 is in terms of the ratio (%) to the mass of the biologically/physiologically active substance loaded on the stent main body.

Comparative Example

First, a 1.0 wt % solution of ethylene-vinyl acetate (vinyl acetate: 40%) in tetrahydrofuran (THF) was prepared, to which dexamethazone and paclitaxel were added in an amount of 30 wt % based on the ethylene-vinyl acetate copolymer, to prepare a solution.

The solution was sprayed onto a stainless steel (SUS316L) stent main body, to prepare a sample. In this case, the thickness of the polymer layer was 10 μm.

The stent thus obtained was served to a sustained release test of the biologically/physiologically active substances in the same manner as in Example 1.

The results are shown in Table 1. Incidentally, the release amount of the biologically/physiologically active substance in Table 1 is in terms of the ratio (%) to the mass of the biologically/physiologically active substance loaded on the stent main body.

TABLE 1

| Lapse of days | Name of medicament | Example 1 | Example 2 | Comp. Example |
|---|---|---|---|---|
| 1st day | Dexamethasone | 81.1 | 86.6 | 80.4 |
| | Paclitaxel | 1.6 | 3.1 | 71.8 |
| | Simvastatin | — | 0.3 | — |
| 3rd day | Dexamethasone | 95.9 | 98.7 | 99.7 |
| | Palitaxel | 6.7 | 7.2 | 96.7 |
| | Simvastatin | — | 0.9 | — |
| 7th day | Dexamethasone | 99.2 | 98.3 | 99.4 |
| | Paclitaxel | 48.9 | 41.4 | 99.1 |
| | Simvastatin | — | 1.6 | — |
| 14th day | Dexamethasone | 98.9 | 96.9 | 99.5 |
| | Paclitaxel | 82.4 | 85.9 | 99.8 |
| | Simvastatin | — | 5.9 | — |
| 28th day | Dexamethasone | * | * | * |
| | Paclitaxel | 99.3 | 98.7 | * |
| | Simvastatin | — | 55.2 | — |
| 60th day | Dexamethasone | * | * | * |
| | Paclitaxel | * | 99.1 | * |
| | Simvastatin | — | 88.3 | — |

Note *: Not measured.

The present invention is not limited to the details of the above-described preferred embodiments. The scope of the invention is defined by the appended claims and all changes and modifications as fall within the equivalence of the scope of the claims are therefore to be embraced by the invention.

What is claimed is:

1. A stent to be implanted in a lumen in a living body, said stent comprising a hollow cylindrical stent main body which is open at both terminal end portions thereof and extends in the longitudinal direction between said two terminal open portions, and a polymer layer provided on a surface of said stent main body, wherein said polymer layer comprises a first biologically/physiologically active substance, and first nano- or micro-capsules composed of a first biodegradable polymer and comprising a second biologically/physiologically active substance therein, and said second biologically/physiologically active substance is released after said first biologically/physiologically active substance is released to the exterior of said stent.

2. The stent according to claim 1, wherein the polymer constituting said polymer layer is a water- or water vapor-permeable polymer.

3. The stent according to claim 1, wherein said stent main body is formed of a metallic material.

4. The stent according to claim 1, wherein said stent main body is formed of a polymeric material.

5. The stent according to claim 1, wherein the polymer constituting said polymer layer is at least one selected from the group consisting of silicone-based polymers, vinyl-based polymers, cellulose-based polymers, polyurethane, polyesters, acrylic polymers, thermoplastic elastomers, biodegradable polymers, and bio-derived polymers.

6. The stent according to claim 1, wherein said first biodegradable polymer composing said first nano- or micro-capsules is at least one selected from the group consisting of polylactic acid, polyglycolic acid, polycaprolactone, polyhydroxy butyrate, and copolymers thereof.

7. The stent according to claim 1, wherein said first biologically/physiologically active substance and said second biologically/physiologically active substance are different from each other.

8. The stent according to claim 1, wherein said first and second biologically/physiologically active substances each comprise at least one selected from the group consisting of carcinostatic agent, immunosuppressant, antibiotic, antirheumatic, antithrombic agent, antihyperlipemic agent, ACE inhibitor, calcium antagonist, integrin inhibitor, antiallergic agent, antioxidant, GPIIb IIIa antagonist, retinoid, flavonoid, carotenoid, lipid improver, DNA synthesis inhibitor, tyrosine kinase inhibitor, antiphlogistic, bio-derived material, and interferon.

9. A stent to be implanted in a lumen in a living body, said stent comprising a hollow cylindrical stent main body which is open at both terminal end portions thereof and extends in the longitudinal direction between said two terminal open portions, and a polymer layer provided on a surface of said stent main body, wherein said polymer layer comprises a first biologically/physiologically active substance, first nano- or micro-capsules composed of a first biodegradable polymer and comprising a second biologically/physiologically active substance therein, and second nano- or micro-capsules composed of a second biodegradable polymer being lower than said first biodegradable polymer in degradation rate and comprising a third biologically/physiologically active substance therein, and said second biologically/physiologically active substance is released after said first biologically/physiologically active substance is released to the exterior of said stent, said third biologically/physiologically active substance is released after said second biologically/physiologically active substance is released.

10. The stent according to claim 9, wherein the polymer constituting said polymer layer is a water- or water vapor-permeable polymer.

11. The stent according to claim 9, wherein said stent main body is formed of a metallic material.

12. The stent according to claim 9, wherein said stent main body is formed of a polymeric material.

13. The stent according to claim 9, wherein the polymer constituting said polymer layer is at least one selected from the group consisting of silicone-based polymers, vinyl-based polymers, cellulose-based polymers, polyurethane, polyesters, acrylic polymers, thermoplastic elastomers, biodegradable polymers, and bio-derived polymers.

14. The stent according to claim 9, wherein said first and second biodegradable polymers each comprise at least one selected from the group consisting of polylactic acid, polyglycolic acid, polycaprolactone, polyhydroxy butyrate, and copolymers thereof.

15. The stent according to claim 9, wherein said first, second and third biologically/physiologically active substances are different from each other.

16. The stent according to claim 9, wherein said first, second and third biologically/physiologically active substances each comprise at least one selected from the group consisting of carcinostatic agent, immunosuppressant, antibiotic, antirheumatic, antithrombic agent, antihyperlipemic agent, ACE inhibitor, calcium antagonist, integrin inhibitor, antiallergic agent, antioxidant, GPIIb IIIa antagonist, retinoid, flavonoid, carotenoid, lipid improver, DNA synthesis inhibitor, tyrosine kinase inhibitor, antiphlogistic, bio-derived material, and interferon.

17. The stent according to claim 9, wherein said first biologically/physiologically active substance is a biologically/physiologically active substance for suppressing thrombus deposition and reducing inflammation, said second biologically/physiologically active substance is a biologically/physiologically active substance for restraining the propagation of smooth muscle cells, and said third biologically/physiologically active substance is a biologically/physiologically active substance for promoting NO production and blood vessel endothelial cell adhesion, whereby a lesion of a blood vessel where the stent is implanted can be maintained in an open state.

18. The method of manufacturing a stent according to claim 1, comprising the steps of: dispersing said first biologically/physiologically active substance and said nano- or micro-capsules composed of said first biodegradable polymer and comprising said second biologically/physiologically active substance therein, in a liquid-state polymer; bringing a surface of said stent main body into contact with said liquid-state polymer; and substantially fixing said polymer to said stent main body.

* * * * *